(12) United States Patent
Kido et al.

(10) Patent No.: US 8,389,029 B2
(45) Date of Patent: Mar. 5, 2013

(54) DETERIORATION SMELL INHIBITOR AND ANTIMICROBIAL

(75) Inventors: Hirotsugu Kido, Kanagawa-ken (JP); Shigeo Il, Kanagawa-ken (JP)

(73) Assignees: Mitsubishi Chemical Corporation, Tokyo (JP); Mitsubishi-Kagaku Foods Corporation, Tokyo (JP)

(*) Notice: Subject to any disclaimer, the term of this patent is extended or adjusted under 35 U.S.C. 154(b) by 0 days.

(21) Appl. No.: 13/546,011

(22) Filed: Jul. 11, 2012

(65) Prior Publication Data

US 2012/0276038 A1 Nov. 1, 2012

Related U.S. Application Data

(62) Division of application No. 12/596,717, filed as application No. PCT/JP2008/001067 on Apr. 23, 2008, now abandoned.

(30) Foreign Application Priority Data

Apr. 27, 2007 (JP) ................................. 2007-119688

(51) Int. Cl.
*A01N 65/00* (2009.01)
(52) U.S. Cl. ...................................... 424/725
(58) Field of Classification Search ........................ None
See application file for complete search history.

(56) References Cited

U.S. PATENT DOCUMENTS

| 7,863,350 | B2 | 1/2011 | Brander et al. |
| 2003/0185946 | A1 | 10/2003 | Il et al. |
| 2008/0044540 | A1 | 2/2008 | Kido |
| 2009/0022824 | A1 | 1/2009 | Akhil |

FOREIGN PATENT DOCUMENTS

| EP | 0 843 965 A1 | 5/1998 |
| JP | 06-303952 | 11/1994 |
| JP | 409215485 | 8/1997 |
| JP | 10-70965 | 3/1998 |
| JP | 10-212489 | 8/1998 |
| JP | 2000-178581 | 6/2000 |
| JP | 2000-198950 | 7/2000 |
| JP | 2000-212597 | 8/2000 |
| JP | 2000-234097 | 8/2000 |
| JP | 2000-234098 | 8/2000 |
| JP | 2000-282081 | 10/2000 |
| JP | 2000-282089 | 10/2000 |
| JP | 2000-290691 | 10/2000 |
| JP | 2001-161335 | 6/2001 |
| JP | 2001-181154 | 7/2001 |
| KR | 2003015512 | 2/2003 |
| WO | WO 01/06876 | 2/2001 |
| WO | WO 2006/116817 A1 | 11/2006 |

OTHER PUBLICATIONS

International Search Report for PCT/JP2008/001067, mailed Aug. 5, 2008.
Ban et al., "Antifungal compostion comprises preset amount of acylated glycerol, mixture of fragrance and/or natural essential oil water forming azeotrope and water", Database WPI, Jan. 15, 2003, XP003003735.
Supplementary European Search Report in EP 08 73 8635 dated Sep. 30, 2010.
English translation of Chinese Office Action CN200880013326.0 received Apr. 10, 2012.

*Primary Examiner* — Michael Meller
(74) *Attorney, Agent, or Firm* — Nixon & Vanderhye P.C.

(57) ABSTRACT

The object of the present invention is to provide a deterioration smell inhibitor capable of effectively inhibiting deterioration smell generating form various products such as foods and cosmetics. The present invention relates to a deterioration smell inhibitor comprising a plant extract and isothiocyanate. As preferred embodiments, the plant extract is a labiatae plant extract, further the labiatae plant extract is an oil-insoluble labiatae plant extract, still further the weight ratio of the oil-insoluble labiatae plant extract/isothiocyanate is 1/1 to 99/1. In other preferred embodiments, the plant extract is a terpenoid alcohol or terpenoid ketone, further the weight ratio of the terpenoid alcohol or terpenoid ketone/isothiocyanate is 0.4/1 to 40/1.

1 Claim, No Drawings

DETERIORATION SMELL INHIBITOR AND ANTIMICROBIAL

This application is a divisional of application Ser. No. 12/596,717 filed Feb. 3, 2010 now abandoned which in turn is the U.S. national phase of International Application No. PCT/JP2008/001067 filed 23 Apr. 2008, which designated the U.S. and claims priority to JP Application No. 2007-119688 filed 27 Apr. 2007, the entire contents of each of which are hereby incorporated by reference.

TECHNICAL FIELD

The present invention relates to deterioration smell inhibitor and antimicrobial. More particularly the present invention relates to a deterioration smell inhibitor and antimicrobial capable of effectively inhibiting deterioration smell generating form for example foods.

BACKGROUND ART

From the announcement of investigation report of Environmental Dispute Coordination Commission, in complaints to pollution, the number of smell pollution complaints is second larger number after the number of noise pollution complaints, and the solution thereof is recently an important subject. An interest for the environmental problem and health effect of environment is increased. Therefore, complaints to bad smells whose degree are not a pollution problem previously are increased so that in a factory neighboring residential area, countermeasures to bad smells are focused.

On the other hand, in general household, complaints to bad smells become constant problems, and an interest for removing bad smells such as foul smell and musty smell is increase. Further, in the art of cleaning agents used in clothes washing and dishes cleaning, there has been actively studied and techniques of using a plant essence as a deodorant substrate have been reported.

For instance, there have been proposed deodorant cleaning agents containing specific plant essences (refer to Patent Documents 1 to 4), a cleaning agent for sterilization and deodorant composition containing a specific surfactant and plant essence (refer to Patent Document 5), deodorant cleaning agents containing specific fragrance components (refer to Patent Documents 6 and 7) and a deodorant cleaning agent containing a fungicide other than plant essences and fragrance components (refer to Patent Document 8).

However, in these, for instance, in case of liquid cleaning agent for dishwasher, this technique is used for a method of removing smells derived from foods such as raw fishes. A sponge or the like used as a dish cleaning tool are placed on condition of containing water for long time so that in this condition, bacterial growth are promoted and a fishy smell derived from the bacteria generates. It is difficult to prevent such fishy smell generation derived from the bacteria by the above deodorant techniques.

In order to prevent the smell derived from the bacteria, it is considered to use an antimicrobial in combination and many antimicrobials used for the liquid cleaning are known. Of these, a technique using a zinc compound as an antimicrobial is known. For instance, it is known that a liquid cleaning agent composition containing an antimicrobial is proposed and as zinc is effective as the fungicide (refer to Patent Document 9). Further, a technique of antimicrobial deodorant cleaning wax has been proposed and it is known that zinc is effective as a metal having antimicrobial activity or deodorant activity (refer to Patent Document 10).

However, the inhibiting activity of deterioration smell by the inorganic compounds such as zinc and silver and plant essences is still not sufficient.

Meanwhile, an isothiocyanate (isothiocyanic ester) has excellent antimicrobial activity and is preferred in view of food sanitation. However, since it has an irritating smell (volatilizing smell) generated by volatilizing thereof, there is a bar to directly add the isothiocyanate to foods.

Patent Document 1: Japanese Patent Application Laid-Open (KOKAI) No. 2000-282089
Patent Document 2: Japanese Patent Application Laid-Open (KOKAI) No. 2000-212597
Patent Document 3: Japanese Patent Application Laid-Open (KOKAI) No. 2000-234098
Patent Document 4: Japanese Patent Application Laid-Open (KOKAI) No. 2000-234097
Patent Document 5: Japanese Patent Application Laid-Open (KOKAI) No. 2000-178581
Patent Document 6: Japanese Patent Application Laid-Open (KOKAI) No. 2000-290691
Patent Document 7: Japanese Patent Application Laid-Open (KOKAI) No. 2000-282081
Patent Document 8: Japanese Patent Application Laid-Open (KOKAI) No. 10-212489
Patent Document 9: Japanese Patent Application Laid-Open (KOKAI) No. 2001-181154
Patent Document 10: Japanese Patent Application Laid-Open (KOKAI) No. 2000-198950

DISCLOSURE OF THE INVENTION

Problem to be Solved by the Invention

The present invention has been made from the above problem. An object of the present invention is to provide a deterioration smell inhibitor capable of effectively inhibiting deterioration smell generating form various products such as foods and cosmetics. Further, the other object of the present invention is to provide a antimicrobial. Still further, the other object of the present invention is to provide a volatilization inhibitor for an isothiocyanate.

Means for Solving the Problem

To solve the above technical subject, the present inventors have sought a material to inhibit deterioration smell from natural products, and as a result, the present invention of deterioration smell inhibitor and antimicrobial comprising a plant extract and isothiocyanate in combination have been accomplished. Also, the present invention of volatilization inhibitor for an isothiocyanate comprising a plant extract as an active ingredient has been accomplished.

Effect of the Invention

According to the deterioration smell inhibitor according to the present invention, it can be prevented to generate deterioration smell from various products such as foods and cosmetics. According to antimicrobial according to the present invention, it can be prevent the bacterial growth in various product although containing an isothiocyanate, while preventing the irritating smell (volatilizing smell) generated by volatilizing thereof. Further, by using the volatilization inhibitor for an isothiocyanate according to the present invention, it is possible to use an isothiocyanate by adding it directly to a food.

PREFERRED EMBODIMENTS FOR CARRYING OUT THE INVENTION

First, in order to clarify the meaning of deterioration smell inhibitor according to the present invention, the difference between the deterioration smell inhibitor and a deodorant is explained.

Deodorizing means not to generate a smell as it is. Namely, from the view of definition of term, a smell as it is of product (especially foods) is prevented and the smell generating naturally from the product is also eliminated (deodorized). On the other hand, deterioration smell inhibiting means not only preventing the smell generating naturally from the product but also a deterioration smell different from the smell generating naturally from the product is prevented while maintaining the smell generating naturally from the product. Further generalizing it, there is a product practically having a smell even though it has naturally no smell. For example, although a plastic has theoretically no smell of polymer, there are impurities other than the polymer as the generation source of smell and this smell is considered as the deterioration smell of plastic. Namely, the term of deterioration smell may be defined as a smell other than the smell generating naturally from the product (smell of decomposed matter and smell generating by oxidizing deterioration or a smell generating across the ages, while maintaining the smell generating naturally from the product. Further, in many case, the decomposition and oxidizing deterioration of product are initiated by bacterial growth so that the deterioration smell inhibitor acts as an antimicrobial.

<Deterioration Smell Inhibitor and Antimicrobial>

The deterioration smell inhibitor and antimicrobial comprises a plant extract and isothiocyanate. In the following description, the deterioration smell inhibitor is explained as a typical example. However, the following explanation is also applied to the embodiment of antimicrobial unless otherwise specified.

(Plant Extract)

The material plant used in the present invention is not specified and there are exemplified various plants such as rosemary, lemongrass, spearmint, mint, sage, thyme and ginger, preferably labiatae plants such as perilla, green perilla, sage, thyme, oregano, red perilla, rosemary (*Rosmarinus officinalis* L.), especially preferably rosemary. Further, in the present invention, an oil-insoluble plant extract is preferred as the plant extract. Accordingly, in the present invention, an oil-insoluble extract of labiatae plant (especially rosemary) is especially preferred. From the labiatae plants, various diterpenes are extracted.

As the terpenes, there are monoterpenes, sesquiterpenes and diterpenes. Concretely, there are exemplified linalool, isoborneol, bornane-2-one, bornane-2,3-dione, fenchan-2-ol, fenchan-2-one, p-menthane-3-ol, p-menthane-1(6),8-diene-2-ol, p-mentha-1,8-diene-7-ol, p-mentha-1-en-8-ol, p-menthane-3-one, p-mentha-1(6),8-diene-2-one, p-mentha-l-en-3-one, p-mentha-4(8)-en-3-one, pin-2-en-7-one, pin-2-en-4-one, thujan-3-one, or the like. In the present invention, these monoterpenoid alcohols or monoterpenoid ketones can be preferably used. Further, in the present invention, it is also preferable to use diterpenoid alcohols such as rosmarinic acid, carnosol, carnosic acid, rosmanol, epirosmanol, epiisorosmanol, rosmarinicdiol and luteolin. Of these, rosmarinic acid, carnosol and carnosic acid are preferred. The above terpenoid alcohols or terpenoid ketones may be synthesized products.

Rosmarinic acid is one of phenolcarboxylic acids and is especially contained in rosemary. The structure of rosmarinic acid is a structure bonding two phenolcarboxylic acids. Therefore, in view of the structure and function, rosmarinic acid has more phenolic hydroxyl groups than that of phenolcarboxylic acids such as ferulic acid, coffeic acid and chlorogenic acid so that antioxidant effect is more excellent. Further, rosmarinic acid has high active effect of enzyme inhibition which is provided to SOD (superoxide dismutase). Also, rosmarinic acid has high inhibition effect for photo-deterioration because of having a conjugated double bond in the structure. The used rosmarinic acid in the present invention is preferably an extract from a natural product, more preferably an extract from rosemary containing rosmarinic acid in large amount.

As a general production method of rosmarinic acid is as follows. As the material thereof, any of whole rosemary herb, or its leaf, root, stem, flower, fruit and seed may be used and preferably its leaf is used. Usually, in order to enhance the extraction effect, chopped up leaves thereof are used. Rosmarinic acid is obtained as a water-soluble extract of rosemary. Therefore, it is obtained by treating the extraction with water containing ethanol, precipitating a water-insoluble component by adding water to the extraction liquid, separating the water-insoluble component and condensing the remained solution under reduced pressure. As the water containing ethanol, one having water content of 40 to 60% by weight is preferably used.

Carnosol and carnosic acid are contained in labiatae plant extract-based spice such as sage, thyme and oregano in large amount. The structure thereof is different from the other antioxidants and has an abietane structure having an isoprene backbone. The antioxidant effect thereof for oil and fats is dramatically stronger than that of other antioxidants. Also, carnosol and carnosic acid has high inhibition effect for photo-deterioration because they have a conjugated double bond in the structure and the structure is easily changed to a radical stabilization structure by having a tautomeric structure even though being subject to a radical attack generated by photo.

The used carnosol and carnosic acid in the present invention are preferably extracts from natural products. These natural products are obtained by extracting from labiatae plant such as sage, thyme and oregano. An extract from rosemary containing rosmarinic acid in large amount is preferable.

One example of production method of carnosol and carnosic acid is shown as follows. First, similar to the above-mentioned water-soluble extract, they are extracted with water containing ethanol, a water-insoluble component is precipitated by adding water to the extraction liquid, active carbon is added and stirred, the water-insoluble component and active carbon are separated to obtain a mixture, the mixture is treated by extracting with ethanol to obtain extraction liquid, and ethanol is removed from the extraction liquid to obtain of carnosol and carnosic acid as a powdery condensed product. The detailed production method thereof may be referred to Japanese Patent Publication 59-4469.

(Isothiocyanate)

Isothiocyanate is a pungent component of for example mustard and wasabi and is natural product obtained from plant extracts so that its level of safety for humans is so high. Isothiocyanate is preferably used for the purpose of food sanitation because it exhibits excellent antibacterial action. Incidentally, the volatile oily antibacterial product is not specified to the natural product and may be a synthesized product as it is by a known method.

As concrete examples of isothiocyanates (isothiocyanates), there are exemplified allyl isothiocyanate, methyl isothiocyanate, ethyl isothiocyanate, propyl isothiocyanate, isopropyl isothiocyanate, butyl isothiocyanate, isobutyl isothiocyanate, isoamyl isothiocyanate, benzyl isothiocyanate, cyclohexyl isothiocyanate, or the like.

(Other Components)

When using the deterioration smell inhibitor according to the present invention, sorbitan esters and natural emulsifiers (lecithins) including polyglyceryl fatty acid esters such as polyglyceryl laurate, polyglyceryl myristate, polyglyceryl palmitate, polyglyceryl stearate and polyglyceryl oleate, sucrose fatty acid esters such as sucrose laurate, sucrose myristate, sucrose palmitate, sucrose stearate and sucrose oleate, or the like may be used in combination. Further, sugars, sugar alcohols, water-soluble antioxidants may be used therewith.

(Deterioration Smell Inhibitor and Antimicrobial)

The deterioration smell inhibitor and antimicrobial according to the present invention are produced by mixing the above respective components. The mixing order is not specified. The weight ratio of the plant extract/isothiocyanate is selected from the following wide ratio range. In case of using the oil-insoluble labiatae plant extract as the plant extract, the weight ratio of the oil-insoluble labiatae plant extract/isothiocyanate is usually 1/1 to 99/1, preferably 2/1 to 95/5, more preferably 3/1 to 9/1. In case of using the terpenoid alcohol or terpenoid ketone as the plant extract, the weight ratio of the terpenoid alcohol or terpenoid ketone/isothiocyanate is usually 0.4/1 to 40/1.

Usually, one of formulations of deterioration smell inhibitor according to the present invention is a solution dissolving the above respective components into water or a mixed solvent of ethanol-water. As the other formulations, there is exemplified a powder produced by spray-drying or freeze-drying the above solution. In case of powder formulation, according to an ordinary method, various additives such as diluents may be used.

The deterioration smell inhibitor according to the present invention may be used as a shape exerting an extended-releasability. For example, a water-soluble film-forming agent such as cyclodextrin, gum arabic, gelatin, hemicellulose, microbial productivity polysaccharides and modified starch, and if required, a powder diluent are dissolved and/or dispersed into water, thereafter the deterioration smell inhibitor according to the present invention is emulsifying-treated therewith, and the obtained emulsified liquid is spray-dried to form powders so that a hygroscopic capsule particle enclosing the deterioration smell inhibitor is produced and it can release the deterioration smell inhibitor under a prescribed humidity or more. When emulsifying, an emulsifier may be used, if required.

As described above, the deterioration smell inhibitor according to the present invention can be used as various formulations such as solution, emulsified formulation, powder and other optional formulations as usage. Also, it may be optionally flavored as usage.

(Addition to Product)

As lower-processed foods, there are exemplified perishable foods, fishery processed products, livestock processed products and greengrocery (nuts and strawberry for process). As medium-processed foods, there are exemplified oil and fat products (liquid oil and fat, frying oil and dressing oil), solid oil and fat products (lard and other animal oil and fats, cacao oil and mixed products) emulsions, margarines, milk products (milk (condensed milk and concentrated milk), cheeses, creams, recombined milk), milled flours (wheat flour, sweetened mixed flours, sugar-free mixed flours) and seasonings (seafood extracts, meat extracts, amino acids, yeast extracts, soy sauce, miso, mayonnaises and spice extracts). As higher-processed foods, there are exemplified breads (bread doughs, flour pastes, sweet bean jams, jams, oil and fats for bread and creams), confectionery products (fried snacks, baked confectioneries, rice confectioneries, cookies, biscuits, semi-baked cakes, unbaked cakes, unbaked Japanese cakes and butter creams), noodles (fried noodles, non-fried noodles, non-boiled noodles, liquid soup, sauces, powder soup, noodle sauces, dried ingredients and retort ingredients), beverages (milk added beverages, fruit juice added beverages, color added beverages, flavor added beverages and plant extract added beverages), livestock meals (hams and sausages, hamburgers and patties), materials for eating (curry, stew, pasta sauces and retort Chinese foods), frozen meals and fried products.

As feeds, there are exemplified fish meals, chicken meals, pork meals, beef meals or the like. As etiquette products, there are exemplified products for toothbrushing, gums, candies and products for bad breath prevention. Namely, the deterioration smell inhibitor according to the present invention can be used for the smell generating from one's oral. As preventing smell relating to daily products, there are exemplified prevention of air contaminant, prevention of smell of toilet and cigarettes or the like. The deterioration smell inhibitor according to the present invention can be used for every smells in a living environment. Further, The deterioration smell inhibitor according to the present invention can be used for cloths attaching these smells, foot smell or the like.

As air cleaner products, there are exemplified air cleaners for domestic use and air cleaners (purification systems) used for autos, ships, electric trains, airplanes and buildings. The deterioration smell inhibitor according to the present invention can be used for smell generating at the on/off action thereof, during the operation thereof and further across the ages.

As the types of contaminated soil, the deterioration smell inhibitor according to the present invention can be used for all soils such as clay, silt, sand, gravel and sediment and is intended to contamination generating bad smell in the small amount presence thereof. For example, leaking gasoline is known in many gas stations. Even though the concentration of gasoline in soil is less than the qualitative lower limit (namely, not detectable, less than 10 mg/kg or 20 mg/kg by tetrachloromethane-IR absorption method), bad smell of gasoline is generated and sensed. As the contaminants to be deodorized, gasoline, kerosene, gas oil and heavy oil.

To the auto products, the deterioration smell inhibitor according to the present invention can be used for deodorant of smell in a new car. Concretely, the deterioration smell inhibitor can be used for deodorant of smell generating by adhering polymer parts each other and by aged deterioration. As examples of concrete type thereof, there are mentioned car interior covers, a dashboard, an air conditioner outlet and floor parts around foot.

To the fishery and livestock processed products, the deterioration smell inhibitor according to the present invention can be used for deodorant of smell generating from various fishes, chicken, pork, beef, or the like, generating at the process thereof and generating during the storage thereof.

To the plastic products, the deterioration smell inhibitor according to the present invention can be used for deodorant of smell generating from polymerized products generated by polymerization and additives used for plastics. As the concrete plastics, there are exemplified hydrocarbon chain polymers such as polyethylene, polypropylene, polybutadiene and polystyrene, copolymers such as polyethylene terephthalate, nitrogen-containing polymers, sulfur-containing polymers and chlorine-containing polymers.

As the home electrical appliances, there are typically exemplified a washing machine, air conditioner and refrigerator. The deterioration smell inhibitor according to the present invention can be used for deodorant of smell of inside of washing machine tub in case of washing machine generating smell at use, smell generating from the inside of air conditioner in case of air conditioner, and smell of inside of refrigerator in case of refrigerator. Further, The deterioration smell inhibitor can be used for smell after use.

To the construction products, the deterioration smell inhibitor according to the present invention can be used for deodorant of smell generating from building materials, smell of plasticizers used for interior materials, and smell generating from the reaction of plasticizer used in the process of construction.

The added amount of deterioration smell inhibitor according to the present invention is usually 0.001 to 30% by weight, preferably 0.01 to 10% by weight, more preferably 0.05 to 5% by weight as the ratio of total amount of plant extract and isothiocyanate to a product.

<Volatilization Inhibitor for an Isothiocyanate>

The volatilization inhibitor for an isothiocyanate according to the present invention comprises a plant extract as an active ingredient. As the plant extract, there can be used the plant extracts explained in the above description of the deterioration smell inhibitor including preferable embodiment. As the volatilization inhibitor for an isothiocyanate, an oil-insoluble extract of labiatae plant (especially rosemary) is preferred. Especially, it is preferable for use of the rosemary extract to remove hexanal (volatile organic compound having an aldehyde group in the molecule) which is a specific smell of rosemary extract. Removing the bad smell components such as hexanal can be easily conducted by extraction treatment using a solvent having relative permittivity (25° C.) of not more than 3 (for example, toluene). The detailed procedure can be referred to the description of Japanese patent application Laid-Open (KOKAI) No. 2004-204212.

In case where the plant extract is used as the volatilization inhibitor for an isothiocyanate, the used amount of plant extract cannot be specified commonly because it should be defined by user's intention about how extent the irritating smell (volatilizing smell) generated by volatilization of the isothiocyanate should be inhibited. However, there is no problem to use the plant extract in large amount, also it may be possible to select the amount within the same range to the case of composition of deterioration smell inhibitor (antimicrobial) according to the present invention. Namely, in case where the an oil-insoluble extract of labiatae plant is used as the plant extract, the ratio of an oil-insoluble extract of labiatae plant/isothiocyanate (weight ratio) is usually 1/1 to 99/1, preferably 2/1 to 95/5, more preferably 3/1 to 9/1. In case where the terpenoid alcohol or terpenoid ketone is used, the ratio of the terpenoid alcohol or terpenoid ketone/isothiocyanate (weight ratio) is usually 0.4/1 to 40/1.

Incidentally, when the ratio of oil-insoluble extract of labiatae plant/isothiocyanate (weight ratio) is 1/1, 1 to 20% of volatile component of isothiocyanate is reduced, and when the ratio is 10/1 (weight ratio), 20 to 70% of volatile component of isothiocyanate is reduced. When the ratio is higher than that, about 99% of volatile component of isothiocyanate is reduced. The volatile components can be by a head space gas chromatography.

EXAMPLES

The present invention is described in more detail by the following examples, but these examples are only illustrative and not intended to limit a scope of the present invention.

<Deterioration Smell Inhibitor>

(Production of Oil-Insoluble Rosemary Extract)

To 1 kg of rosemary, 10 L of 50% water-containing ethanol was added, heat-refluxed for three hours and filtered at the warming condition to obtain a filtrate. The residue was further subjected to extraction treatment twice with 6 L 50% water-containing ethanol to obtain a further filtrate. These obtained filtrates were mixed and 5 L of water was added into the mixed filtrate to precipitate a precipitate. Into this, 100 g of active carbon was added, and the mixture was stirred for 1 hour, preserved at a cold place overnight, and filtered to obtain a filtrate A. Further, to 1 kg of rosemary, 10 L of 50% water-containing ethanol was added, heat-refluxed for three hours and filtered at the warming condition to obtain a filtrate. The residue was further subjected to extraction treatment twice with 6 L 50% water-containing ethanol to obtain a further filtrate. These obtained filtrates were mixed and 5 L of water was added into the mixed filtrate to precipitate a precipitate. Into this, 100 g of active carbon was added, and the mixture was stirred for 1 hour, preserved at a cold place overnight, and filtered to obtain a mixture of precipitate and active carbon. Into the mixture, 4 L of ethanol was added, heat-refluxed for three hours and filtered at the warming condition to obtain a filtrate. The residue was further subjected to extraction treatment twice with 2.4 L ethanol to obtain a filtrate B. The filtrate A and filtrate B were mixed and concentrated under reduced pressure to obtain a powdery oil-insoluble rosemary extract.

(Isothiocyanate)

As the isothiocyanate, isothiocyanic acid allyl ester natural product ("mustard essential oil" manufactured by VOX TRADING CO., LTD.) having purity of 97% or more was used.

(Preparation of Formulation)

First, by using the above oil-insoluble rosemary extract and isothiocyanate, each solution (A and B) shown in Tables 1 and 2 was prepared. By using these solutions, each sample of deterioration smell inhibitor shown in Table 3 was prepared and the inhibiting ability of deterioration smell was evaluated. The sensory evaluation was conducted by six monitors and the evaluation results are shown as an average evaluation. The smaller the average evaluation value is, the higher the deodorant activity is thereby less smell.

TABLE 1

| (A: oil-insoluble rosemary extract solution: RM solution) | |
| --- | --- |
| Oil-insoluble rosemary extract | 2 parts by weight |
| Ethanol | 70 parts by weight |
| Water | 28 parts by weight |

TABLE 2

| (B: isothiocyanate solution: AIT solution) | |
| --- | --- |
| Isothiocyanate | 5 parts by weight |
| Vegetable fat and oil | 1 part by weight |
| Polyglyceryl fatty acid ester | 2.4 parts by weight |
| Water | 91.6 parts by weight |

TABLE 3

|  | Oil-insoluble rosemary extract solution | Isothiocyanate solution |
| --- | --- | --- |
| Sample 1 | 1 | 0.05 |
| Sample 2 | 1 | 0 |
| Sample 3 | 0 | 0.05 |

<Experiment 1: Model Bad Smell Inhibiting Test>

Generally, the components constituting bad smell are aldehydes, acids, amines or thiols. Then, based on this, acetaldehyde, nonenal, butyric acid, valeric acid, dimethylamine and dimethylsulfide are selected as the components constituting bad smell, and 1 ppm (20 μg/20 ml) solutions of each component was prepared. 2 ml of each solution was sampled and mixed to prepare model materials of bad smell. Into the each model material of bad smell, 20 μl of deterioration smell inhibitor was dropped and mixed, respectively. The sensory deodorant evaluation was conducted based on additive free case as the reference and the evaluation criterion as shown in Table 4. The results are shown in Table 5.

TABLE 4

| (Evaluation criterion) | |
| --- | --- |
| 1 | The bad smell is neutralized. |
| 2 | The bad smell is slightly remained. |
| 3 | The bad smell is remained |
| 4 | The bad smell is almost remained. |
| 5 | No change. |

TABLE 5

Results of bad smell inhibiting test for the model material

|  | Deterioration smell inhibitor | Sensory deodorant evaluation |
| --- | --- | --- |
| Example 1 | Sample 1 | 1.1 |
| Comp. Example 1 | Sample 2 | 3.1 |
| Comp. Example 2 | Sample 3 | 3.1 |
| Comp. Example 3 | Febreze (manufactured by P & G) | 4.5 |
| Comp. Example 4 | Additive free | 5 |

(Experiment 2: Inhibiting Test of Smell Fishy of Shrimp)

An iced block of shrimps (1.8 kg) was thawed with running water and dipped with the samples of deterioration smell inhibitors as shown in Table 3. Thereafter, it was washed and boiled. The sensory deodorant evaluation was conducted based on additive free shrimp case as the reference and the evaluation criterion as shown in Table 6. The results are shown in Table 7.

TABLE 6

| (Evaluation criterion) | |
| --- | --- |
| 1 | When getting the monitor's mouth around and chewing the shrimp, no smell fishy of shrimp was smelled. |
| 2 | When getting the monitor's mouth around and chewing the shrimp, smell fishy of shrimp was slightly smelled. |
| 3 | When getting the monitor's mouth around the shrimp, no smell fishy of shrimp was smelled, however when chewing the shrimp, smell fishy of shrimp was smelled. |
| 4 | When getting the monitor's mouth around the shrimp smell fishy of shrimp was slightly smelled, and when chewing the shrimp, smell fishy of shrimp was smelled. |
| 5 | When getting the monitor's mouth around the shrimp smell fishy of shrimp was smelled. |

TABLE 7

Results of inhibiting test of smell fishy of shrimp

|  | Deterioration smell inhibitor | Sensory deodorant evaluation |
| --- | --- | --- |
| Example 1 | Sample 1 | 1.1 |
| Comp. Example 1 | Sample 2 | 3.3 |
| Comp. Example 2 | Sample 3 | 3.5 |
| Comp. Example 3 | "Yuushin" (manufactured by Mitsubishi-Kagaku Foods Corporation) | 4.1 |
| Comp. Example 4 | Additive free | 5 |

(Experiment 3: Smell Inhibiting Test of Contaminated Soil With Paraffinum Liquidum)

The each deterioration smell inhibitor solution was diluted ten times with water and added to contaminated soil with petroleum oil to conduct the sensory deodorant evaluation. The sensory deodorant evaluation was conducted by comparing a case of contaminated soil with petroleum oil without additive. The evaluation was conducted based on the evaluation criterion as shown in Table 8 and the results are shown in Table 9.

TABLE 8

| (Evaluation criterion) | |
| --- | --- |
| 1 | Petroleum smell was deodorized. |
| 2 | Petroleum smell was slightly smelled. |
| 3 | No change |

TABLE 9

<Results of smell inhibiting test of contaminated soil with paraffinum liquidum>

|  | Deterioration smell inhibitor | Sensory deodorant evaluation |
| --- | --- | --- |
| Example 1 | Sample 1 | 1 |
| Comp. Example 1 | Sample 2 | 2.4 |
| Comp. Example 2 | Sample 3 | 2.5 |
| Comp. Example 3 | Additive free | 3 |

(Gas Chromatography Analysis)

10 g of each soil used in the above sensory deodorant evaluation was put into a sample tube and was subjected to a measurement of head space gas chromatography ("Agilent6890 GC") to evaluate the strength of smell of aliphatic hydrocarbons and aromatic hydrocarbons, causing the smell of contaminated soil. The evaluation was conducted by comparing a case of contaminated soil with petroleum oil without additive as 100. The results are shown in Table 10

TABLE 10

(Comparing the strength of smell)

|  | Deterioration smell inhibitor | Aliphatic hydrocarbons | Aromatic hydrocarbons |
| --- | --- | --- | --- |
| Example 1 | Sample 1 | 0.48 | 2.7 |
| Comp. Example 1 | Sample 2 | 5.9 | 14.5 |
| Comp. Example 2 | Sample 3 | 22.3 | 19.0 |
| Comp. Example 3 | Additive free | 100 | 100 |

As seen from the results shown in Table 10, by addition of sample 1, both aliphatic hydrocarbons and aromatic hydrocarbons, causing the smell of contaminated soil were reduced. From this, it is clearly understood that the deterioration smell inhibitor according to the present invention has a highly beneficial effect on deterioration smell inhibiting.

<Antimicrobial and Volatilization Inhibitor for an Isothiocyanate>

An antimicrobial comprising oil-insoluble rosemary extract and isothiocyanate was prepared and subjected to antimicrobial activity test. Further, at that time, the irritating smell (volatilizing smell) generated by volatilization of the isothiocyanate was evaluated to evaluate the activity as the volatilization inhibitor for an isothiocyanate by the comprising oil-insoluble rosemary extract.

As the oil-insoluble rosemary extract and isothiocyanate, the materials used in the above preparation of deterioration smell inhibitor were used. As the oil-insoluble rosemary extract, the formulated RM solution was used. Further, an oil-insoluble rosemary extract prepared by the following method (low smell product) was formulated and used as the RM solution.

(Preparation of Oil-Insoluble Rosemary (Low Smell Product))

An oil-insoluble rosemary extract was obtained by the same method described in the above "Preparation of oil-insoluble rosemary extract" to obtain an oil-insoluble rosemary extract, thereafter 1 kg of the obtained oil-insoluble rosemary extract was dispersed into 1.1 kg of hexane (relative permittivity (25° C.): 1.90) and stirred for 1 hour at ordinary temperature. Thereafter, hexane was filtered away and the remained product was dried to obtain an oil-insoluble rosemary extract (low smell product).

(Preparation of Formulated Product)

First, using the above prepared oil-insoluble rosemary extract (low smell product), a solution shown in Table 11 was prepared.

TABLE 11

(A: oil-insoluble rosemary extract (low smell product) solution: RM solution)

| | |
|---|---|
| oil-insoluble rosemary extract (low smell product) | 2 parts by weight |
| Ethanol | 70 parts by weight |
| Water | 38 parts by weight |

(Antimicrobial)

By using the above oil-insoluble rosemary extract formulated solution and isothiocyanate, samples of antimicrobial shown in Table 12 were prepared.

TABLE 12

| | Oil-insoluble rosemary extract solution | Oil-insoluble rosemary extract (low smell product) | Isothiocyanate solution |
|---|---|---|---|
| Sample 1 | 1 | 0 | 0.05 |
| Sample 3 | 0 | 0 | 0.05 |
| Sample 4 | 0 | 1 | 0.05 |

(Antimicrobial Activity Test)

The antimicrobial activity test was conducted according to the method described in Japanese Patent Application Laid-Open (KOKAI) No. 11-322521. Namely, a fungus liquid where Escherichia coli JCM1649 was cultivated to grow in Brain-Heart infusion broth (BHI) culture medium (manufactured by Nippon Suisan Kaisha, Ltd) at 37° C. overnight, was prepared and diluted with sterilized phosphate buffer to prepare a test fungus liquid containing Escherichia coli JCM1649 in an amount of $10^5$/ml. On the other hand, each above sample 1, 3 and 4 was used, diluted with water to prepare aqueous solutions having isothiocyanate concentrations of 5, 10, 25, 50 and 100 ppm. Into 10 ml of the respective aqueous isothiocyanate solutions having respective isothiocyanate concentration, 1 ml of test fungus liquid was added, respectively. Simultaneously, a test liquid was prepared by adding 1 ml of test fungus liquid into 10 ml of water without isothiocyanate as a control test. The respective prepared test fungus liquids were heated to 37° C. for 10 minutes, chilled in ice and was subjected to pour culture in a desoxycolate culture medium (manufactured by Nippon Suisan Kaisha, Ltd) at 37° C. so that the generation status of colony was observed after 24, 48 and 72 hours. The same results were obtained in the samples 1, 3 and 4. The results are shown in Table 13.

TABLE 13

(Antimicrobial activity test: *E. coli*)

| | Concentration of isothiocyanate (ppm) | | | | |
|---|---|---|---|---|---|
| | 5 | 10 | 25 | 50 | 100 |
| Antimicrobial activity (Samples 1, 3 and 4) | X | ○ | ○ | ○ | ○ |

(X: No antimicrobial activity, ○: Having antimicrobial activity)

(Volatilization Inhibiting Activity Test for an Isothiocyanate)

The above prepared antimicrobial samples 1, 3 and 4 were used and diluted with water to prepare aqueous solutions of isothiocyanate having its concentration of 5, 10, 25 50 and 100 ppm. The sensory evaluation of irritating smell (volatilizing smell) by volatilization of isothiocyanate was conducted by six monitors based on the evaluation criterion as shown in Table 14. The evaluation results are shown in Table 15 as an average evaluation. The smaller the average evaluation value is, the higher the deodorant activity is thereby less volatilizing smell.

TABLE 14

(Evaluation criterion)

| | |
|---|---|
| 1 | Smell of isothiocyanate was deodorized. |
| 2 | Smell of isothiocyanate was slightly remained |
| 3 | Smell of isothiocyanate was remained |
| 4 | Almost smell of isothiocyanate was remained |
| 5 | No change |

TABLE 15

(Results of volatilization inhibiting activity test for an isothiocyanate)

| | Concentration of isothiocyanate (ppm) | | | | |
|---|---|---|---|---|---|
| | 5 | 10 | 25 | 50 | 100 |
| Sample 1 | 2.4 | 2.6 | 3 | 3.6 | 4.6 |
| Sample 3 | 4 | 5 | 5 | 5 | 5 |
| Sample 4 | 1.5 | 2.1 | 2.3 | 3.0 | 4.4 |

As seen from the results of antimicrobial activity shown in Table 13 and results of volatilization inhibiting activity test for an isothiocyanate shown in Table 15, it is clearly understood that the irritating smell (volatilizing smell) by volatilization of isothiocyanate is inhibited, while maintaining the excellent antimicrobial activity of isothiocyanate.

The invention claimed is:
1. A volatilization inhibitor consisting essentially of a rosemary extract and isolated isothiocyanate in a weight ratio of rosemary extract to isolated isothiocyanate of 3:1 to 9:1.

* * * * *